United States Patent [19]

Browning

[11] Patent Number: 5,143,939

[45] Date of Patent: Sep. 1, 1992

[54] METHOD OF TREATING SOIL AND AGRICULTURAL CROPS FOR CONTROLLING WORMS AND NEMATODES

[76] Inventor: Henry A. Browning, Rte. 1, Box 90, Quitman, Ga. 31643

[21] Appl. No.: 719,015

[22] Filed: Jun. 21, 1991

Related U.S. Application Data

[60] Division of Ser. No. 459,273, Dec. 29, 1989, Pat. No. 5,026,734, which is a continuation-in-part of Ser. No. 297,185, Jan. 12, 1989, abandoned.

[51] Int. Cl.$^5$ ............................................. A01N 31/14
[52] U.S. Cl. ...................................................... 514/723
[58] Field of Search ........................................ 514/723

[56] References Cited

U.S. PATENT DOCUMENTS

| | | | |
|---|---|---|---|
| 3,930,010 | 12/1975 | Klopping | 514/388 |
| 3,930,030 | 12/1975 | Klopping | 514/338 |
| 3,984,570 | 10/1976 | Bent et al. | 514/723 |
| 4,212,870 | 7/1980 | Gibb | 546/304 |
| 4,227,911 | 10/1980 | Leonard et al. | 71/77 |
| 4,497,831 | 2/1985 | Lover et al. | 514/717 |

FOREIGN PATENT DOCUMENTS 1604859 12/1981 United Kingdom.

OTHER PUBLICATIONS

Tergitol Publications: Overview and Product Information, Specialty Nonionic Surfactants, Nonionic Surfactants: 15-S-9, 15-S-3, 15-S-5, 15-S-7, 15-S-20, 15-S-30 and 15-S-40.

*Primary Examiner*—Allen J. Robinson
*Attorney, Agent, or Firm*—Dowell & Dowell

[57] ABSTRACT

This invention relates to the discovery that a very particular kind of nonionic surfactant, namely an alkyloxypolyethyleneoxyethanol can be used as the sole active ingredient to control fungus, mites, worms, termites, nematodes and other insects. It is believed that these alkyloxypolyethyleneoxyethanols can be represented by the formula:

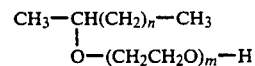

wherein n is from 9 to 15 and m is from 3 to 40.

9 Claims, No Drawings

METHOD OF TREATING SOIL AND AGRICULTURAL CROPS FOR CONTROLLING WORMS AND NEMATODES

CROSS-REFERENCE TO RELATED APPLICATIONS

This application is a divisional application of Ser. No. 07/459,273 filed Dec. 29, 1989, now U.S. Pat. No. 5,026,734 issued Jun. 25, 1991, which is a continuation-in-part application of Ser. No. 07/297,185 filed Jan. 12, 1989, now abandoned.

BACKGROUND OF THE INVENTION

Most of the pesticides in use today are expensive toxic chemicals that must be carefully applied and frequently monitored in order to insure that their toxic residues do not get into the food chain or otherwise harm either humans, animals or the environment. My discovery provides substantial benefits over the toxic chemicals that have heretofore been used in that the use of the alkyloxypolyethyleneoxyethanols of the present invention are not injurious to plants, do not disturb the biological balance and do not possess the undesirable pollution aspects inherent in the use of so many known pesticides.

SUMMARY OF THE INVENTION

This invention relates to the discovery that a very particular kind of nonionic surfactant, namely an alkyloxypolyethyleneoxyethanol can be used as the sole active ingredient to control fungus, mites, worms, termites, nematodes and other insects. It is believed that these alkyloxypolyethyleneoxyethanols can be represented by the formula:

$$CH_3-CH(CH_2)_n-CH_3$$
$$|$$
$$O-(CH_2CH_2O)_m-H$$

wherein n is from 9 to 15 and m is from 3 to 40.

DESCRIPTION OF THE PREFERRED EMBODIMENT

The aforementioned alkyloxypolyethyleneoxyethanols are biodegradable nonionic surfactants consisting of a mixture of ethoxylates of secondary alcohols having from 9 to 15 carbon atoms in the aliphatic hydrophobic chain, and which have an average of 3 to 5, 7, 9, 12, 15, 20, 30 or 40 moles of ethylene oxide, respectively in the hydrophillic entity. Materials which correspond to the compositions are available commerically as TERGITOL 15-S series of ethylene oxide derivatives manufactured by Union Carbide Corporation(i.e. 15-S-3, 15-S-5, 15-S-7, 15-S-9, 15-S-12, and 15-S-15.) One method for the manufacture of such nonionic surface active agents is believed to be set forth in U.S. Pat. No. 2,870,220 of Union Carbide. A blend or combination of these secondary alcohol ethoxylates such as TERGITOL 15-S-3 added to TERGITOL 15-S-9 results in clear, easily handled materials for application. Of the available ethoxylates of secondary alcohols, TERGITOL 15-S-9 is preferred. As indicated above, it is understood that these nonionic surfactants can be represented by the formula:

$$CH_3-CH(CH_2)_n-CH_3$$
$$|$$
$$O-(CH_2CH_2O)_m-H$$

where n is from 9 to 15 and m is from 3 to 40.

Union Carbide characterizes its above TERGITOLS with the empirical formula:

$$C_{11-15}H_{23-31}O(CH_2CH_2O)_xH$$

in its Material Safety Data Sheets.

The above nonionic surfactants in the same instances can be applied to targets (buildings, soils, etc.) in technical strength if desired. However, because of the active nature of the secondary alcohol ethoxylates, it is recommended that they be admixed with a suitable carrier, this is especially true when applied to targets such as plants, foilage and animals. Suitable inexpensive carriers that are preferred are either water or vegetable oil. Other more expensive carriers can also be used. In accordance with my invention, the above nonionic surfactants are applied in an amount of approximately 8 oz. to about 16 oz. per acre. The amount of water or vegetable oil used as the carrier can vary considerably as long as about 8 oz. to about 16 oz. of the nonionic surfactant is applied to the plants per acre. Because vegetable oil is capable of forming a much finer mist than is possible with water, a substantially less volume of oil can be used with the surfactant compared to the same amount of surfactant in water.

The following examples are presented for the purpose of further illustrating and explaining the present invention and are not to be taken as limiting in any regard.

EXAMPLE 1

| TERGITOL 15-S-9 | 16.0 oz. |
|---|---|
| Water | 250.0 gallons |
| | 250.16 - total solution in gallons |

This solution was sprayed on mature citrus trees with severe rust mite infestation. A rate of 250.16 gallons of solution per treated acre was used with temperatures in the low 60° F. range. After three days, the only detectable rust mites to be found were "inside" the canopy of the dense foliage of the trees. Only carcasses of dead mites were detected in over 98% of those trees inspected. Depending upon the type of spray application, tests indicated that solutions including as little as 15 gallons of water could be applied per acre and be effective.

EXAMPLE 2

| TERGITOL 15-S-9 | 8.0 oz. |
|---|---|
| Water | 5.0 gallons |

This solution was applied to one acre of cotton severely infested with bollworms of approximately ¼ inch to 1/64 of an inch in length by means of fixed-wing aircraft. Within twenty minutes of application only bollworms one inch in length or larger were found alive in the field.

EXAMPLE 3

| TERGITOL 15-S-9 | 8.0 oz. |
|---|---|
| Vegetable oil | 32.0 oz. |
| | 40.0 oz. total solution |

This solution was applied to cotton infested with bollworms, aphids and spider mites at the rate of 40.0 oz. per acre by means of a fixed-wing aircraft. Within twenty minutes of application, no live pests were found.

EXAMPLE 4

| TERGITOL 15-S-9 | 8.0 oz. |
|---|---|
| Water | 1-2 gallons |

This solution was applied to the floor of a residential kitchen in a semi-tropical area of Florida. It was noted that brown spiders, and two other types of insects, carpenter ants and a centipede died after being placed in contact with the wet floor within 10 minutes of contact.

EXAMPLE 5

| TERGITOL 15-S-9 | 1.0 oz. |
|---|---|
| Water | 5-20.0 gallons |

This solution was used as a "bath" for a dog which had been in contact with ticks and fleas found in hunting areas in south Georgia. After being place in the bath container for a period of several minutes, no live parasitic insects were found on the dog.

EXAMPLE 6

| TERGITOL 15-S-9 | 8.0 oz. |
|---|---|
| Water | 5.0 gallons |

This solution was applied to peanuts during one entire production year. No other fungicide was applied until two weeks prior to digging. At that point the product BRAVO was applied at recommended rates. There was no leaf spot present when the fungicide BRAVO was applied. No additional insecticide was used during the production year to the acreage treated with the surfactant. The yield on the test areas was in excess of 1.75 tons/acre.

EXAMPLE 7

| TERGITOL 15-S-9 | 8.0 oz. |
|---|---|
| Water | 5.0 gallons |

This solution was applied to an area of a building foundation where termites were found. The solution was injected into the termite bed area beneath the surface of the soil. After a twelve hour period, the "bed" area under and around the infested area was excavated. All termites found, were dead. No other fumigant was used.

EXAMPLE 8

| TERGITOL 15-S-9 | 2.0 oz. |
|---|---|
| Water | 15.0 gallons (minimum) |

This solution was sprayed around shrubs and ornamental flowers of a south Georgia residence, where mosquitos were present in large numbers. Spraying resulted in killing of the pests, with no reinfestation for a period of three days. Stronger solutions of TERGITOL may result in leaf damage.

EXAMPLE 9

A plot of land was tested and found to have a nematode count of 400 per test soil sample, which made the land unsuitable for raising cotton. In view of the soil unsuitability, peanuts were selected to be planted in the plot. The land was thereafter treated in accordance with my invention by first ground spraying with a solution consisting of TERGITOL 15-S-9 (16 ounces per acre) and water (10-20 gallons per acre) and thereafter tilling. The land was thereafter sprayed with a liquid composition from a plane at a per acre concentration of 8-16 ounces of TERGITOL 15-S-9 and 10-20 gallons of water. Similar applications were made every 6-10 days for several months. At the end of several months another soil test was made and the nematode count was essentially zero per test soil sample. In addition, the peanuts were free of insects and white mold during the entire growing season.

EXAMPLE 10

A plot of land was prepared for cotton by initially ground spraying approximately 16 oz./acre of TERGITOL 15-S-9 with 10-20 gallons of water/acre and then tilling the land. Thereafter the cotton crop was periodically sprayed by air plane utilizing 8-16 oz. TERGITOL 15-S-9 and 3-5 gallons of water/per acre except when small worms were noted and then the TERGITOL 15-S-9 was applied at 8-16 oz. with 26-34 oz. of vegetable oil per acre. The spraying applications were effective in controlling eggs, bollworms, mites, white flies, and aphids.

EXAMPLE 11

Several orange trees in Florida were treated for rust mites by spraying with a solution of approximately 2 oz. of TERGITOL 15-S-9 and approximately 15 gallons of water. The treatment eliminated the rust mite problems.

The surfactant solutions of the present invention have also been tested and found effective for controlling lice on hogs, aphids on roses and pecan trees, mold on pecan trees, fungus on shrubs, and insects on garden and vegetable plants.

In addition to the surfactants of the present invention being useful in controlling fungus, mites, nematodes, worms, mold and other insects, it is believed that the surfactants function as soil neutrilizers. As a result of some of the tests set forth above, it has been noted that the soil ph in the test plots has been increased and remains between approximately 6.5 to less than 7.0 without the use of lime being necessary. In one test plot, several acres of the soil were generally non-productive due to soil ph levels of less than 6.0. After repeated applications of the surfactants as set forth above over an entire test plot, it was noted that the previously unproductive acres became productive. Tests indicated that the ph levels had been raised to above 6.5.

Although my invention has been described in connection with the above examples, it is not limited by these examples and should be construed in connection with the following claims and obvious equivalents thereof. For instance, TERGITOL 15-S-3, 15-S-7, 15-S-12 and 15-S-15 have been used for similar applications and the same rates as set forth in the examples in oil and/or water solutions with similar results being achieved. Therefore, it is believed that the nonionic surfactants of the TERGITOL-15-S series are believed to fall within the scope of the present invention.

I claim:

1. A method of treating soil and agricultural crops for controlling worm or nematode pests which comprises applying to the infected location thereof a pesticidally effective amount of a composition comprising a liquid carrier and at least one nonionic surfactant represented by the formula:

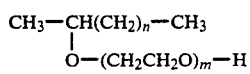

where
n is from 9–15 and
m is from 3–40.

2. The method defined in claim 1 wherein said surfactant is applied in an amount of at least 4 oz. per acre.

3. The method defined in claim 2 wherein n is 15 and m is 9.

4. The method defined in claim 2 wherein said liquid carrier is water.

5. The method defined in claim 2 wherein said liquid carrier is a vegetable oil.

6. The method defined in claim 1 in which said surfactant is applied at the rate of between about 8.0 to 16 oz. per acre together with water as said carrier.

7. The method defined in claim 1 in which said surfactant is applied at the rate of between about 8.0 to 16 oz. per acre together with vegetable oil as said carrier.

8. The method of claim 1 in which said composition is sprayed on plant life and wherein the surfactant is present in an amount not to exceed approximately 1.0 oz. per approximately 7.5 gallons of carrier.

9. The method of claim 8 in which the carrier is water.

* * * * *